United States Patent [19]
le Blanc et al.

[11] Patent Number: 6,123,659
[45] Date of Patent: Sep. 26, 2000

[54] BLOOD PUMP WITH PROFILED OUTFLOW REGION

[75] Inventors: Pieter W. C. J. le Blanc, Citrus Heights; Tracy V. Petersen, Granite Bay; Timothy R. Maher, Orangevale; Kenneth C. Butler, Carmichael, all of Calif.

[73] Assignee: Nimbus Inc., Rancho Cordova, Calif.

[21] Appl. No.: 09/237,724

[22] Filed: Jan. 26, 1999

[51] Int. Cl.[7] .................................................. F04B 17/00
[52] U.S. Cl. ............................................ 600/16; 417/356
[58] Field of Search ................................ 600/16, 17, 18; 417/356; 604/151

[56] References Cited

U.S. PATENT DOCUMENTS

| 4,994,078 | 2/1991 | Jarvik ........................................ 623/3 |
| 5,112,200 | 5/1992 | Isaacson et al. ....................... 417/356 |
| 5,211,546 | 5/1993 | Isaacson et al. ....................... 417/356 |
| 5,527,159 | 6/1996 | Bozeman, Jr. et al. ................ 417/45 |
| 5,707,218 | 1/1998 | Maher et al. ........................... 417/356 |
| 5,890,883 | 4/1999 | Golding et al. ....................... 417/423.12 |

FOREIGN PATENT DOCUMENTS

WO 97/37698 10/1997 WIPO .
WO 98/25657 6/1998 WIPO .

*Primary Examiner*—Scott M. Getzow
*Attorney, Agent, or Firm*—Fish & Richardson P.C., P.A.

[57] ABSTRACT

The invention provides an axial flow blood pump with slanting outflow components. Specifically, the invention provides a blood pump having an angling outer stator blade edge structure in combination with a blood flow conduit having a constricting inner diameter. After constricting, the blood flow conduit can expand such that the inner diameter of the conduit increases. In addition, the blood pump can have an angling inner stator blade edge structure and a tapering stator blade hub or tapering rotor element.

55 Claims, 6 Drawing Sheets

BLOOD PUMP WITH PROFILED OUTFLOW REGION

STATEMENT AS TO FEDERALLY SPONSORED RESEARCH

The U.S. Government has a paid-up license in this invention and the right in limited circumstances to require the patent owner to license others on reasonable terms as provided for by the terms of contract number N01-HV-58155 awarded by the National Institutes of Health.

BACKGROUND

1. Technical Field

The invention relates to axial flow blood pumps having useful stator blade and conduit configurations.

2. Background Information

Axial flow pumps are useful in a variety of fluid pumping applications. A number of implantable axial flow blood pumps, for example, presently are under development for application as either artificial hearts or cardiac assist devices. An axial flow blood pump typically includes a blood flow conduit that defines a cylindrical blood flow channel, an impeller mechanism mounted within the blood flow channel, a rotor coupled to actuate the impeller mechanism for blood pumping action, and an electric motor stator for actuating the rotor by electromagnetic force. The impeller blades can be mounted directly on the rotor. In this case, the rotor may form an elongated member that extends axially along the cylindrical blood flow channel. The impeller blades can be mounted about the rotor, for example, in a spiral-like pattern. Alternatively, the impeller blades can be mechanically coupled to the rotor via a transmission shaft.

An axial flow blood pump typically includes outlet stator blades that redirect rotational blood flow generated by the impeller blades. The outlet stator blades are positioned adjacent the outlet end of the rotor. In some cases, the outlet stator blades can be integrally formed with or attached to a stator hub that supports the outlet end of the rotor. In particular, the stator hub can be configured as a bearing that receives the outlet end of the rotor and supports the rotor for rotation about its longitudinal axis. The stator blades generally extend radially outward from the stator hub to the inner wall of the cylindrical blood flow channel. The outlet stator blades serve to direct the blood flow such that the tangential velocity components are re-oriented in the axial direction.

SUMMARY

The present invention features an axial flow blood pump with slanting outflow components. The term "slanting" as used herein refers generally to structures that are angling, tapering, converging, constricting, or expanding. Specifically, the present invention provides an axial flow blood pump having a stator blade structure with a portion of its outer edge angled toward a longitudinal axis reference extending through a blood flow channel, and a blood flow conduit configuration that constricts such that the inner diameter of the blood flow conduit narrows. It is to be understood that the blood flow conduit can have an inner wall defining a cylindrical or non-cylindrical shape. When the blood flow conduit has an inner wall defining a non-cylindrical shape, the term "inner diameter" can be replaced by the term "inner boundary". Since a rotor element is typically positioned in the center of the blood flow channel, the longitudinal axis upon which the rotor element rotates can be used, for purposes of description, as a longitudinal axis reference that extends through the blood flow channel. Typically, the pump has multiple stator blades arranged about a stator hub such that the angling outer edges of each stator blade converge toward the longitudinal axis reference that extends through the blood flow channel. In addition, the pump can have a stator blade structure with a portion of its inner edge angled toward the longitudinal axis reference extending through the blood flow channel, and a stator hub or rotor element that is tapered in a direction toward an outflow port. In this case, a portion of both outer and inner edges of the stator blade is angled toward the longitudinal axis reference extending through the blood flow channel while the blood flow conduit constricts and the stator hub or rotor element tapers. Together, these slanting outflow components create a gradually expanding cross-sectional blood flow field area within the constricting portion of the blood flow conduit. Specifically, the stator hub or rotor element within the constricting blood flow conduit tapers at a degree greater than the degree of blood flow conduit constriction such that the net result is a blood flow field with an increasing cross-sectional area. The term "blood flow field" as used herein refers to the space available for the flow of blood within the blood pump.

A blood pump in accordance with the invention is capable of achieving a gradual change and reduction in blood flow velocity with a decreased stator blade length. Specifically, a pump with a constricting blood flow conduit, angling outer and inner stator blade edges, and a tapering stator hub or rotor element can achieve the same gradual change and reduction in velocity, but with a shorter axial stator blade distance, as a pump with a longer stator blade. These velocity changes include, without limitation, the re-direction of tangential blood flow, created by the pump's rotating impeller system, to an axial direction as well as the reduction of this axial flow velocity by converting the blood's kinetic energy to static pressure. Gradual changes in these velocities are particularly advantageous since abrupt changes can lead to excessive red blood cell trauma and the generation of thromboemboli. Likewise, any reduction in pump size is advantageous since a smaller implantable device can be less obtrusive to the body and can be maneuvered within the body with more ease than a larger implantable device.

Slanting outflow components also create a well-organized and uniform blood flow field such that regions of stagnation, separation, or recirculation are reduced or eliminated. Such regions would otherwise be conducive to the generation of thromboemboli. In addition, the overall free stream velocity achieved by blood flowing through this configuration is higher than that for other designs, providing additional heat removal capacity at the bearing sites.

Further, the structure of a constricting blood flow conduit and the nature of an angling outer edge of a stator blade facilitates pump manufacture and assembly. Unlike existing pump designs having a blood flow conduit that does not constrict and an outer stator blade edge that is not angled, the blood pumps described herein do not require as precise a diametrical match of the outer edge of a stator blade with the inner wall of a blood flow conduit. Rather, an angling outer stator blade edge when combined with a blood flow conduit having a constricting inner diameter can produce a taper-lock configuration. This taper-lock configuration can reduce the chance of producing gaps or discontinuities between an outer stator blade edge and inner wall of a blood flow conduit. Reducing such gaps and discontinuities is important since they are potential catalysts for generating thromboemboli.

Installation of an angling stator blade structure without producing gaps and discontinuities can be achieved with less challenging manufacturing tolerances and without the need for substantial sliding contact with the inner wall of a blood flow conduit, an operation that could itself result in discontinuities and other material defects. Further, a taper-lock configuration can help prevent longitudinal and rotational movement of a stator blade structure within a blood flow channel during pump operation. For example, the two components can be firmly fixed in a taper-lock configuration with a minimum application of axial load despite the small contact area of an outer stator blade edge. If desired, a taper-lock configuration can be fortified by conventional attachment techniques such as welding, cross-pinning, or set screws.

In general, the invention features an axial flow blood pump having a pump housing, inflow bearing, outflow bearing, electromagnetic rotor element, motor stator element, impeller mechanism, and outflow stator blade. The pump housing has a blood flow conduit with an inflow port for receiving blood and an outflow port for expelling blood. The inflow bearing is disposed within the blood flow conduit at a position proximal the inflow port and the outflow bearing is disposed within the blood flow conduit at a position proximal the outflow port. The electromagnetic rotor element has an inflow end on a side of the electromagnetic rotor element proximal the inflow port, an outflow end on a side of the electromagnetic rotor element proximal the outflow port, and a longitudinal axis extending through the inflow end of the electromagnetic rotor element and the outflow end of the electromagnetic rotor element. The inflow end is rotatably mounted to the inflow bearing and the outflow end is rotatably mounted to the outflow bearing. In addition, the inflow bearing and the outflow bearing support the electromagnetic rotor element for rotation within the blood flow conduit about the longitudinal axis of the electromagnetic rotor element. The motor stator element generates electromagnetic force and is oriented such that the electromagnetic force actuates the electromagnetic rotor element to rotate within the blood flow conduit about the longitudinal axis of the electromagnetic rotor element. The impeller mechanism is coupled to the electromagnetic rotor element such that the impeller mechanism rotates upon actuation of the electromagnetic rotor element. In addition, the impeller mechanism contains a blade structure oriented to facilitate movement of blood from the inflow port to the outflow port of the blood flow conduit upon rotation of the impeller mechanism. The outflow stator blade is disposed within the blood flow conduit and adjacent the outflow end of the electromagnetic rotor element. In addition, the outflow stator blade contains an outer edge disposed on a side of the outflow stator blade proximal an inner wall of the blood flow conduit; an inner edge disposed on a side of the outflow stator blade proximal the longitudinal axis of the electromagnetic rotor element; and a major surface extending from the outer edge of the outflow stator blade to the inner edge of the outflow stator blade. At least a portion of the outer edge of the outflow stator blade extends at an angle toward the longitudinal axis of the electromagnetic rotor element.

In another embodiment, the invention features an axial flow blood pump having a pump housing, inflow bearing, outflow bearing, electromagnetic rotor element, motor stator element, impeller mechanism, and outflow stator blade. The pump housing has a blood flow conduit with an inflow port for receiving blood and an outflow port for expelling blood. In addition, the blood flow conduit has an inner wall defining an inner diameter of the blood flow conduit and at least a portion of the inner diameter of the blood flow conduit constricts. The inflow bearing is disposed within the blood flow conduit at a position proximal the inflow port and the outflow bearing disposed within the blood flow conduit at a position proximal the outflow port. The electromagnetic rotor element has an inflow end on a side of the electromagnetic rotor element proximal the inflow port, an outflow end on a side of the electromagnetic rotor element proximal the outflow port, and a longitudinal axis extending through the inflow end of the electromagnetic rotor element and the outflow end of the electromagnetic rotor element. The inflow end is rotatably mounted to the inflow bearing and the outflow end is rotatably mounted to the outflow bearing. The inflow bearing and the outflow bearing support the electromagnetic rotor element for rotation within the blood flow conduit about the longitudinal axis of the electromagnetic rotor element. The motor stator element generates electromagnetic force and is oriented such that the electromagnetic force actuates the electromagnetic rotor element to rotate within the blood flow conduit about the longitudinal axis of the electromagnetic rotor element. The impeller mechanism is coupled to the electromagnetic rotor element such that the impeller mechanism rotates upon actuation of the electromagnetic rotor element. In addition, the impeller mechanism has a blade structure oriented to facilitate movement of blood from the inflow port to the outflow port of the blood flow conduit upon rotation of the impeller mechanism. The outflow stator blade is disposed within the blood flow conduit and adjacent the outflow end of the electromagnetic rotor element.

The invention also features an axial flow blood pump having a blood flow conduit, rotor element, motor stator, impeller blade, and outflow stator blade. The rotor element has an inflow end, an outflow end, and a longitudinal axis extending through the inflow and outflow ends. In addition, the rotor element is suspended for rotation within the blood flow conduit about the longitudinal axis. The motor stator is oriented to rotate the rotor element. The impeller blade is coupled to the rotor element and oriented to facilitate movement of blood through the blood flow conduit upon rotation of the rotor element. The outflow stator blade is disposed within the blood flow conduit and adjacent the outflow end of the rotor element. In addition, the outflow stator blade has an outer edge disposed on a side of the outflow stator blade proximal an inner wall of the blood flow conduit and an inner edge disposed on a side of the outflow stator blade proximal the longitudinal axis of the rotor element. At least a portion of the outer edge of the outflow stator blade extends at an angle toward the longitudinal axis of the rotor element.

In another embodiment, the invention features an axial flow blood pump having a blood flow conduit, rotor element, motor stator, impeller blade, and outflow stator blade. The blood flow conduit has an inflow port for receiving blood and an outflow port for expelling blood. The blood flow conduit also has an inner wall defining an inner diameter of the blood flow conduit and at least a portion of the inner diameter of the blood flow conduit constricts. The rotor element is oriented to rotate within the blood flow conduit. The motor stator is oriented to rotate the rotor element. The impeller blade is coupled to the rotor element and oriented to facilitate movement of blood through the blood flow channel upon rotation of the rotor element. The outflow stator blade is disposed within the blood flow conduit and adjacent the outflow end of the rotor element.

The details of one or more embodiments of the invention are set forth in the accompanying drawings and the descrip-

DESCRIPTION OF DRAWINGS

Like reference numbers and designations in the various drawings indicate like elements.

DETAILED DESCRIPTION

The present invention involves an axial flow blood pump with slanting outflow components. Specifically, the present invention provides blood pumps having an angling outer stator blade edge structure in combination with a blood flow conduit that constricts such that the inner diameter of the blood flow conduit narrows. After constricting, the blood flow conduit can expand such that the inner diameter of the blood flow conduit increases. In addition, these blood pumps can have an angling inner stator blade edge structure and a tapering stator blade hub or tapering rotor element.

The invention provides outflow components that are slanting such that blood flow can be gradually manipulated with a minimal amount of blood damage. Such outflow components can be incorporated into any type of axial flow blood pump design. For example, diagrams provided herein (FIGS. 1 and 5) depict two different blood pump designs within the scope of the invention that each incorporate slanting outflow components. Other designs incorporating these components also are within the scope of the invention.

The axial flow blood pumps provided herein can be implanted within an animal, e.g., human, to provide the function of an artificial heart or a cardiac assist device. Thus, it is to be understood that each component of an implantable blood pump within the scope of the invention can be constructed from materials compatible with this intended use. For example, the inner wall of a blood flow conduit can be made from an inert biocompatible material that does not interfere with the properties of blood, such as titanium.

Figure 1:
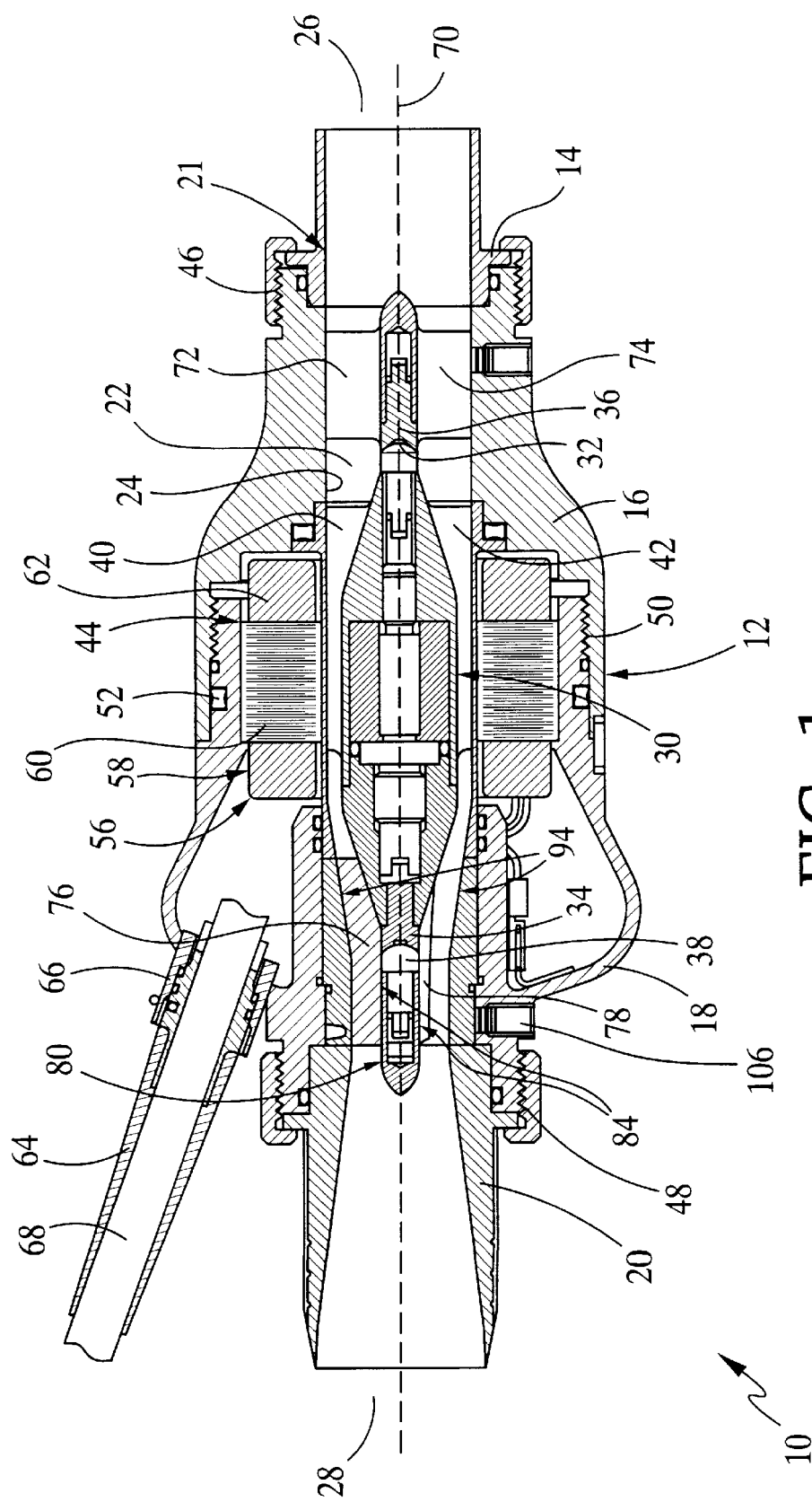
FIG. 1 is a longitudinal cross-sectional diagram of an implantable blood pump having a compact stator hub design that incorporates slanting outflow components.

FIG. 1 is a longitudinal cross-sectional diagram of an implantable blood pump 10 incorporating an angling outer stator blade edge structure with a constricting blood flow conduit in accordance with an embodiment of the present invention. As shown in FIG. 1, pump 10 can have a pump housing 12 having an inflow portion 14, a central portion having a first part 16 and a second part 18, and an outflow portion 20. In addition, pump housing 12 contains a blood flow conduit 21 having an inner wall 24 that defines a generally cylindrical blood flow channel 22. Inflow portion 14 is designed to be joined with the cardiovascular system, and has an inflow port 26 through which blood enters blood flow channel 22. Outflow portion 20 also is designed to be joined with the cardiovascular system, and has an outflow port 28 through which blood exits blood flow channel 22. A rotor element 30 is disposed within and extends axially along blood flow channel 22. Rotor element 30 has an inflow end 32 and an outflow end 34 that are rotatably mounted to inflow bearing 36 and outflow bearing 38, respectively. Briefly, rotor element ends can be rotatably mounted to bearings using a hemispherically shaped ball-and-cup bearing system. For example, a cup-shaped rotor end is rotatably mounted to a ball-shaped bearing or vice versa. Impeller blades 40, 42 are mounted on rotor element 30 and oriented to impart axial flow energy to blood flow upon actuation of rotor element 30. In FIG. 1, only two impeller blades 40, 42 are visible. Rotor element 30, however, can have any number of impeller blades (e.g., one, three, four, or five), each arranged, for example, in a spiral-like pattern. Motor stator assembly 44 can be disposed within pump housing 12 and can be generally annular in shape.

With further reference to FIG. 1, inflow portion 14 can be connected to the central portion via first part 16 using threads 46. Likewise, outflow portion 20 can be connected to the central portion via second part 18 using threads 48. The first and second parts 16, 18 of pump housing 12 can be reciprocally threaded, as indicated by reference numeral 50, such that one is screwed into the other to couple both parts and enclose motor stator assembly 44 and rotor element 30. An o-ring 52 can be incorporated to ensure a leak-resistant fit.

Motor stator assembly 44 contains a motor stator 56. Motor stator 56 can have three or more separate groups of windings, two of which are illustrated in FIG. 1. In particular, FIG. 1 shows a winding group 58 having a metal stamping portion 60 and a set of windings 62 wound about the stamping portion 60. An electrical conduit 64 can be coupled to the second part 18 of the central portion of pump housing 12 via a redundantly sealed connection 66 realized by two or more o-rings. Electrical conduit 64 can carry an electrical cable 68 to motor stator assembly 44 for connection of electrical conductors with respective winding groups. It is to be understood that the connection of electrical conductors with respective winding groups of motor stator 56 is such that an electrical current energizes the respective windings of motor stator 56 to generate electromagnetic field energy for actuation of rotor element 30. The phases of electromagnetic field energy are controlled in a well known manner such that the stator windings are energized sequentially to create a rotating field. Rotor element 30 can carry a permanent magnet that interacts with this rotating field to rotate the rotor about its longitudinal axis 70. The moving rotor thereby actuates impeller blades 40, 42 to impart axial flow energy to the blood flowing through blood flow channel 22.

Inflow stator blades 72, 74 are located within blood flow channel 22 between, for example, inflow port 26 and impeller blades 40, 42. In addition, inflow stator blades 72, 74 can be positioned to contact inner wall 24 and support inflow bearing 36. In FIG. 1, only two inflow stator blades 72, 74 are visible, however, any number of inflow stator blades (e.g., one, three, four, or five) can be arranged around inflow bearing 36 to provide support.

Outflow stator blades 76, 78 are located within blood flow channel 22 between, for example, impeller blades 40, 42 and outflow port 28. For example, outflow stator blades 76, 78 can be adjacent to the outflow end 34 of rotor element 30. In addition, outflow stator blades 76, 78 can be positioned to contact inner wall 24 and support outflow bearing 38 by contacting stator hub 80. In this case, outflow bearing 38 is a part of stator hub 80 and is positioned to face inflow port 26. In FIG. 1, only two outflow stator blades 76, 78 are visible. Specifically, stator blade 76 is shown to project vertically with the page and stator blade 78 is shown to project into the page at a downward slant. In both cases, the outflow stator blades extend radially from longitudinal axis 70 toward inner wall 24. Further, any number of stator blades (e.g., one, three, four, or five) can be arranged about stator hub 80 to provide support for outflow bearing 38.

Figure 2:
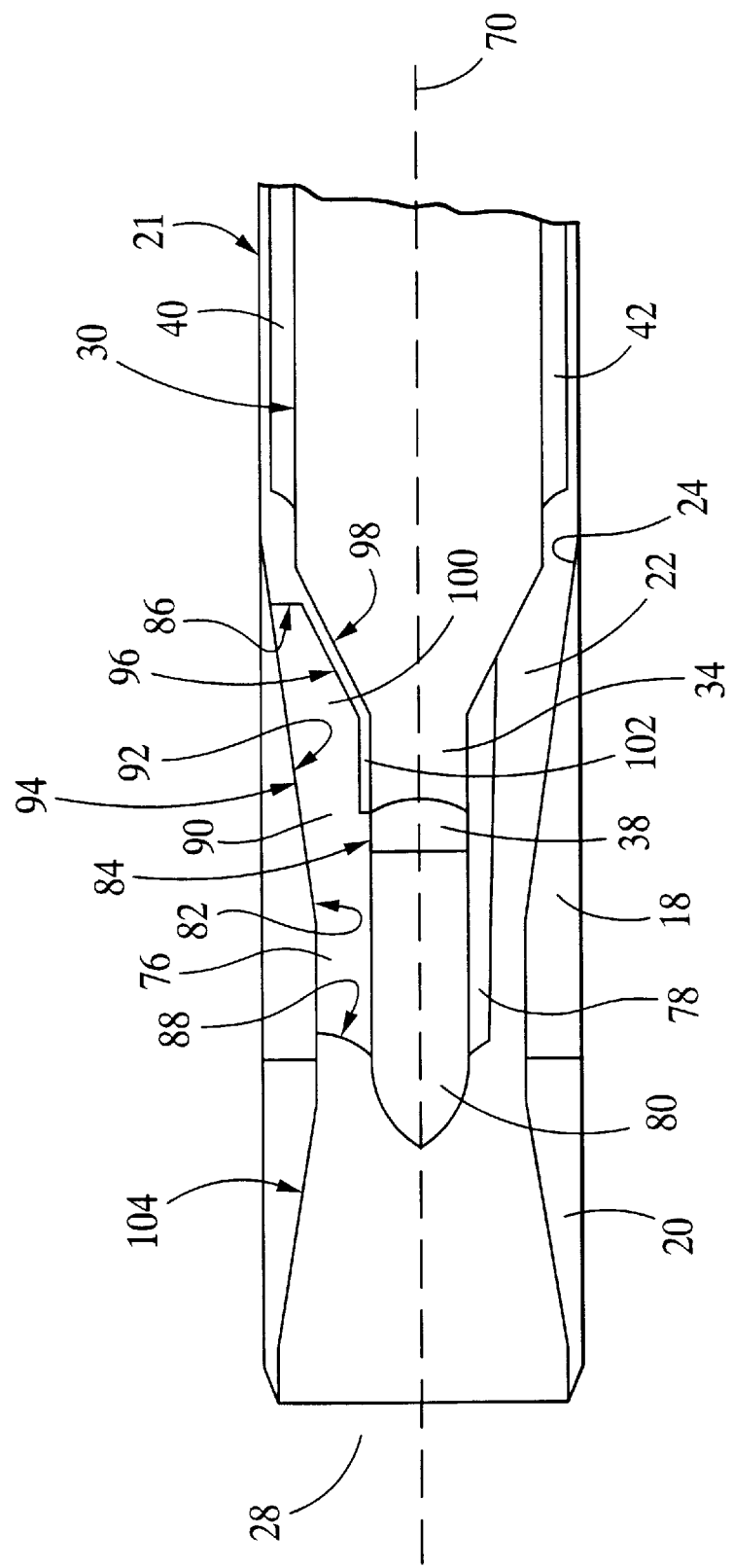
FIG. 2 is an enlarged view of the profiled outflow region of the pump shown in FIG. 1.
Figure 3:
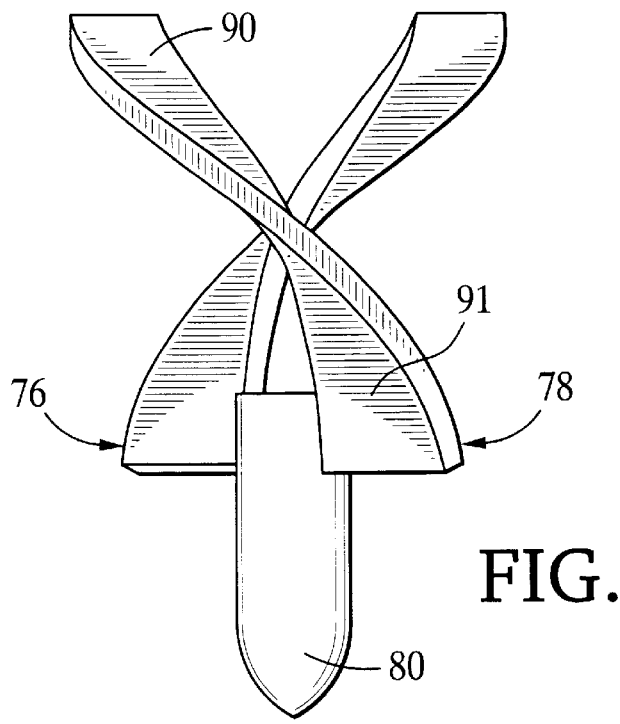
FIG. 3 is a side view diagram of the compact stator hub design shown in FIG. 1, incorporating two stator blades.
Figure 4:
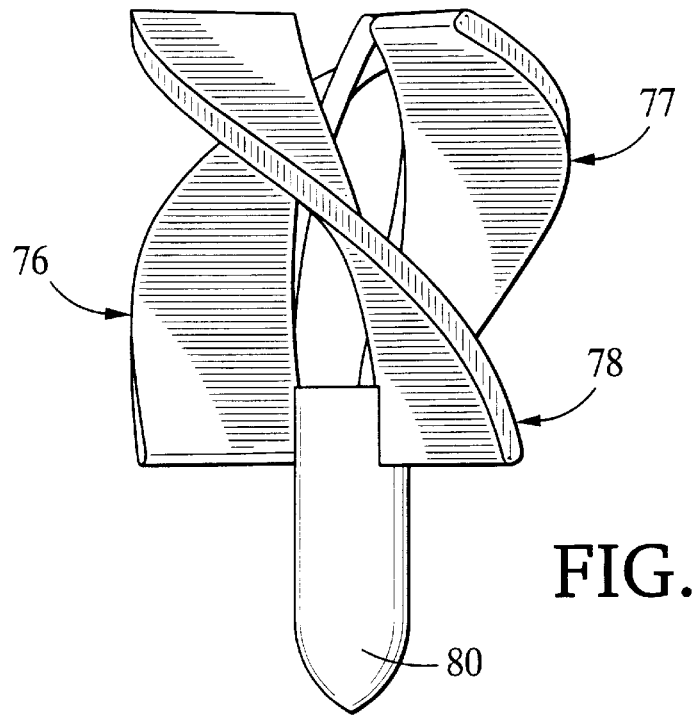
FIG. 4 is a side view diagram of the compact stator hub design shown in FIG. 1, incorporating three stator blades.

FIG. 2 is a diagram depicting an enlarged view of the profiled outflow region of blood flow conduit 21 from FIG. 1. Each outflow stator blade 76, 78 has an outer edge 82 disposed on a side of the blade that is proximal inner wall 24. In addition, each outflow stator blade 76, 78 has an inner edge 84 disposed on a side of the blade proximal longitudinal axis 70; a leading edge 86 disposed on a side of the blade proximal inflow port 26; and a trailing edge 88 disposed on a side of the blade proximal outflow port 28. Further, each outflow stator blade 76, 78 has a major surface 90 extending from outer edge 82 to inner edge 84. At least a portion of this major surface is curved. As shown in FIG. 3, a side view diagram depicting stator hub 80 with two outflow stator blades 76, 78, both major surface 90 and the opposing second major surface 91 of stator blades 76, 78 are curved along their entire length. It is noted that one major surface is often referred to as the pressure side whereas the opposing surface is referred to as the suction side. Such side distinctions depend upon the relationship between the major surface and the direction of the tangential blood flow velocities. In FIG. 3, major surface 90 is the suction side and surface 91 is the pressure side. FIG. 4 is a side view diagram depicting stator hub 80 with three stator blades 76, 77, 78, each having a curved major surface.

The curved major surface of these outflow stator blades serve to direct the flow of blood. With reference to FIG. 1, blood flows in a predominately axial direction from a blood vessel into pump 10 through inflow port 26. As the blood traverses pump 10, the rotation of rotor element 30 and impeller blades 40, 42 increases its overall velocity while changing its direction of flow from an axial direction to a more tangential direction. Before exiting pump 10, however, the curvature of outflow stator blades 76, 78 restores blood flow to a more axial direction. Thus, outflow stator blades 76, 78 are structured and positioned to restore blood flow to a more axial flow orientation.

With further reference to FIG. 2, outer edge 82 contains an angling portion 92 having an angle that extends toward longitudinal axis 70 and in a direction toward outflow port 28. Inner wall 24 contains a constricting portion 94 within second part 18 such that blood flow conduit 21 constricts in that region. The constricting of blood flow conduit 21 can proceed in a direction toward outflow port 28. In addition, the region of blood flow conduit 21 containing constricting portion 94 can contain at least a portion of angling portion 92. For example, angling portion 92 can be within the constricting region of blood flow conduit 21 defined by constricting portion 94.

As also shown in FIG. 2, inner edge 84 can contain an angling portion 96 having an angle that extends toward longitudinal axis 70 and in a direction toward outflow port 28. Rotor element 30 can contain a tapering portion 98 having a taper that proceeds toward longitudinal axis 70 and in a direction toward outflow port 28. Each outflow stator blade also can contain an extending portion 100 that is positioned between rotor element 30 and inner wall 24 while extending upstream from stator hub 80 toward inflow port 26. Extending portion 100 is positioned such that a gap 102 is formed between inner edge 84 of extending portion 100 and rotor element 30. Gap 102 allows rotor element 30 to rotate without interference from outflow stator blades 76, 78. The gap size can remain constant as it approaches outflow bearing 38 or stator hub 80. In addition, the gap can exhibit a step change in size at some distance along outflow bearing 38 or stator hub 80. At least a portion of angling portion 96 can be part of extending portion 100. For example, angling portion 96 defines a portion of inner edge 84 that is part of extending portion 100.

It is noted that the net result of the constricting portion 94 and the tapering portion 98 creates a blood flow field having a cross-sectional area that increases, at least at some point, in the direction toward outflow port 28. This increase in the cross-sectional blood flow field area decreases axial blood flow velocity while increasing static pressure.

As shown in FIG. 2, inner wall 24 can contain an expanding portion 104 within outflow portion 20 such that blood flow conduit 21 expands in that region. The expanding of blood flow conduit 21 can proceed in a direction toward outflow port 28.

Collectively, the angling portion 92 of outer edge 82, constricting portion 94 of inner wall 24, angling portion 96 of inner edge 84, tapering portion 98 of rotor element 30, extending portion 100 of outflow stator blades 76, 78, and expanding portion 104 of inner wall 24 gradually change and reduce blood flow velocities within blood flow channel 22 of pump 10 such that blood damage is minimized. In addition, the overall length of a pump achieving these gradual velocity changes with minimal blood damage can be shorter than the length required for a pump not using the configurations described herein. Specifically, the gradual re-orientation of tangential blood flow is accomplished primarily by the structure and position of stator blades 76, 78. For example, the curved portion of each stator blade 76, 78 forces tangentially moving blood to move in a more axial direction. The gradual reduction of axial blood flow velocity, resulting in a conversion of the blood's kinetic energy to static pressure, is accomplished by the expansion of the cross-sectional area of the blood flow field within blood flow conduit 21 from rotor element 30 to outflow port 28. For example, as the cross-sectional blood flow field area increases, blood flow velocity decreases and static pressures increases. In addition, the blood flow field within this region of blood flow conduit 21 is well-organized and uniform such that regions of stagnation, separation, or recirculation are reduced or eliminated.

Figure 5:
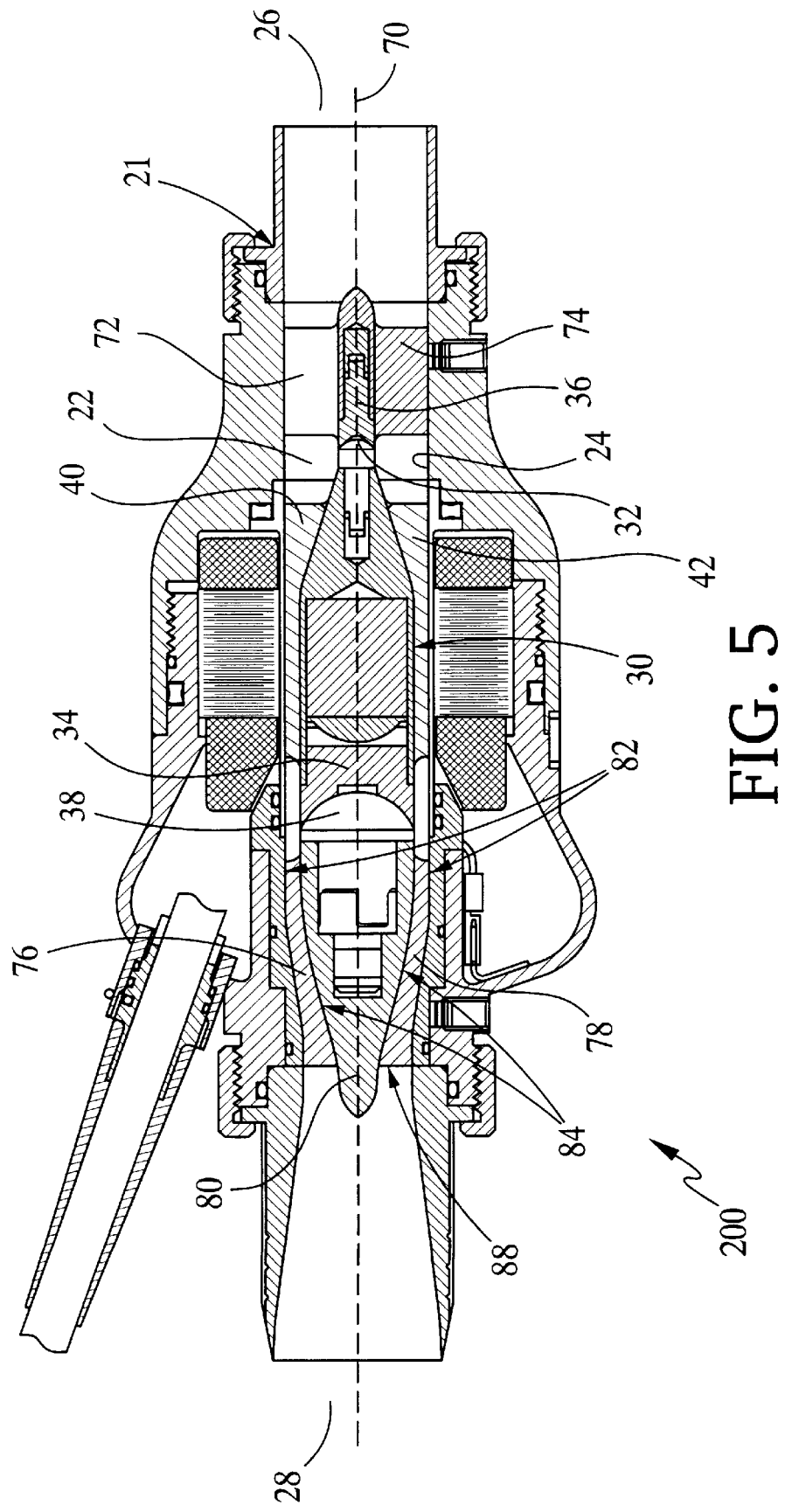
FIG. 5 is a longitudinal cross-sectional diagram of an implantable blood pump having an enlarged stator hub design that incorporates slanting outflow components.

FIG. 5 is a longitudinal cross-sectional diagram of an implantable blood pump 200 incorporating an angling outer stator blade edge structure with a constricting blood flow conduit in accordance with another embodiment of the present invention. Blood pump 200 conforms essentially with blood pump 10 shown in FIG. 1. Thus, descriptions for components not described for pump 200 can be found in the above section describing pump 10.

Like pump 10, pump 200 contains a rotor element 30 disposed within and extended axially along blood flow channel 22. Rotor element 30 can have an inflow end 32 and an outflow end 34 that are rotatably mounted to inflow bearing 36 and outflow bearing 38, respectively. Briefly, rotor element ends can be rotatably mounted to bearings using a hemispherically shaped ball-and-cup bearing system. For example, a cup-shaped rotor end is rotatably mounted to a ball-shaped bearing and vice versa. It is noted that the size of the hemispherically shaped ball-and-cup bearing system can vary as shown by comparing the outflow bearing sizes in FIGS. 1 and 5. Impeller blades 40, 42 can be mounted on rotor element 30 and oriented to impart axial flow energy to blood flow upon actuation of rotor element 30. In FIG. 5, only two impeller blades 40, 42 are visible. Rotor element 30, however, can have any number of impeller blades (e.g., one, three, four, or five) each arranged, for example, in a spiral-like pattern.

With further reference to FIG. 5, inflow stator blades 72, 74 can be located within blood flow channel 22 between, for example, inflow port 26 and impeller blades 40, 42. In addition, inflow stator blades 72, 74 can be positioned to contact inner wall 24 and support inflow bearing 36. In FIG. 5, only two inflow stator blades 72, 74 are visible, however, any number of inflow stator blades (e.g., one, three, four, or five) can be arranged around inflow bearing 36 to provide support.

Outflow stator blades 76, 78 are located within blood flow channel 22 between, for example, impeller blades 40, 42 and outflow port 28. For example, outflow stator blades 76, 78 can be adjacent to the outflow end 34 of rotor element 30. In addition, outflow stator blades 76, 78 can be positioned to contact inner wall 24 and support outflow bearing 38 by contacting stator hub 80. In this case, outflow bearing 38 is a part of stator hub 80 and is positioned to face inflow port 26. Outflow stator blades 76, 78 also extend radially from longitudinal axis 70 toward inner wall 24. In FIG. 5, only two outflow stator blades 76, 78 are visible, however, any number of outflow stator blades (e.g., one, three, four, or five) can be arranged about stator hub 80 to provide support for outflow bearing 38.

Figure 6:
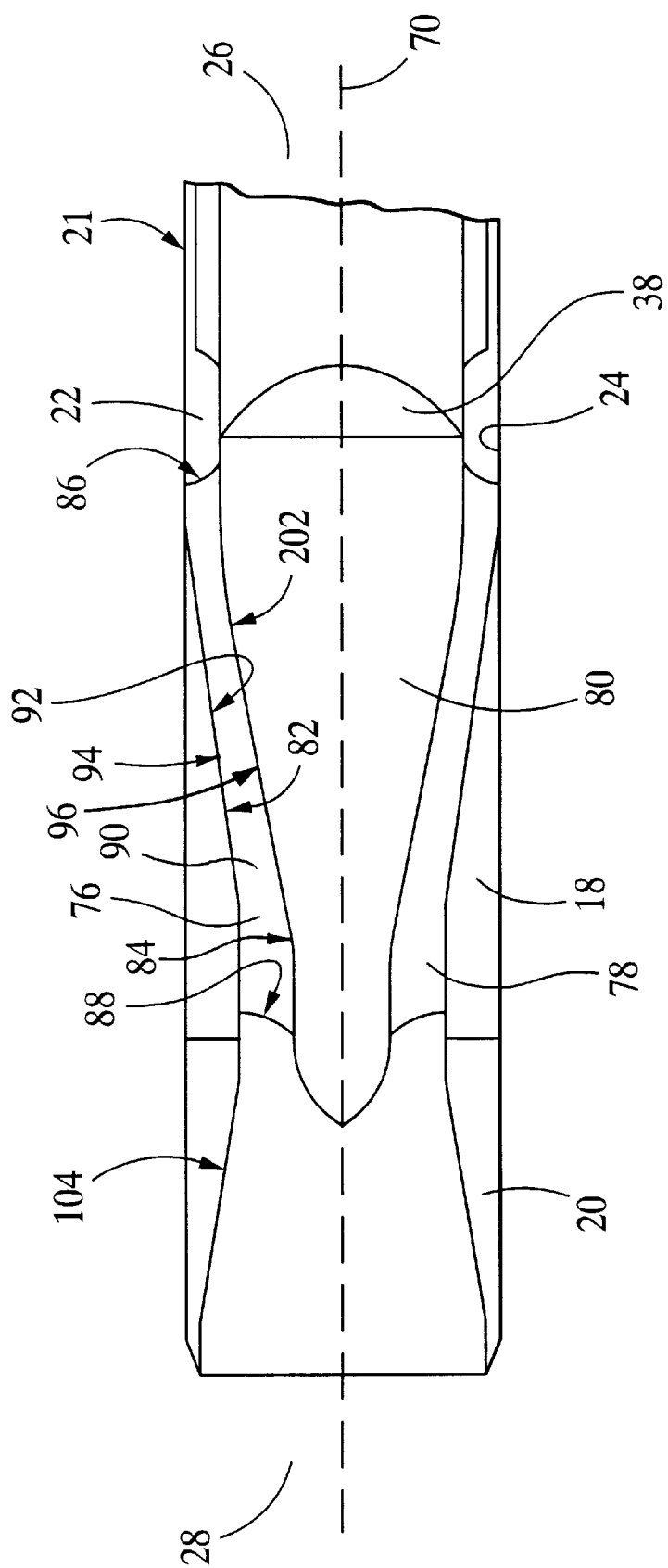
FIG. 6 is an enlarged view of the profiled outflow region of the pump shown in FIG. 5.
Figure 7:
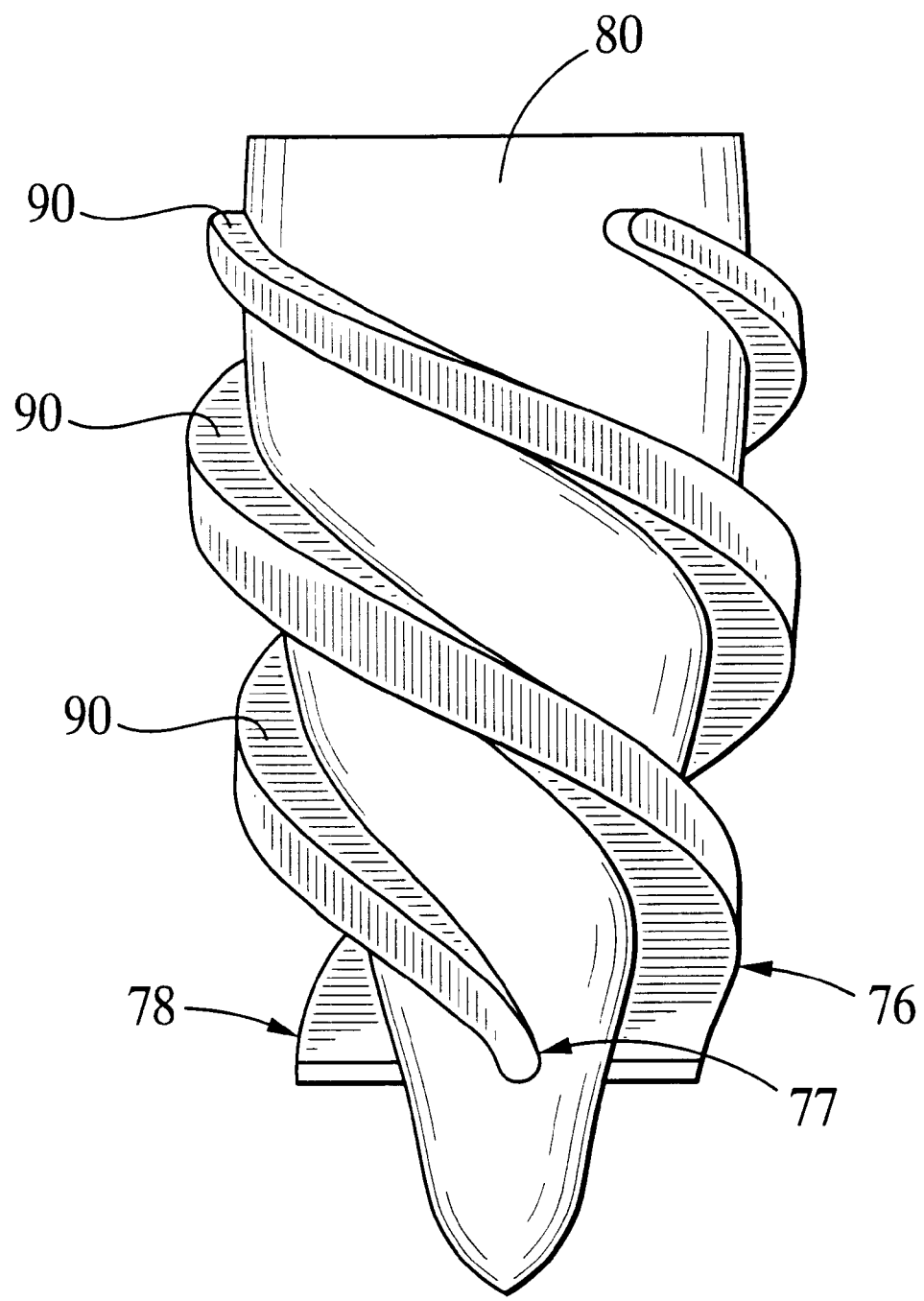
FIG. 7 is a side view diagram of the enlarged stator hub design shown in FIG. 5, incorporating three stator blades.

As shown in FIG. 6, an enlarged view of the outflow region of FIG. 5, each outflow stator blade 76, 78 has an outer edge 82 disposed on a side of the blade that is proximal inner wall 24. In addition, each outflow stator blade 76, 78 has an inner edge 84 disposed on a side of the blade proximal longitudinal axis 70; a leading edge 86 disposed on a side of the blade proximal inflow port 26; and a trailing edge 88 disposed on a side of the blade proximal outflow port 28. Further, each outflow stator blade 76, 78 has a major surface 90 extending from outer edge 82 to inner edge 84. At least a portion of this major surface is curved. As discussed above, the curved major surface of each stator blade serves to re-orient the flow of blood in a more axial direction. FIG. 7 is a side view diagram of stator hub 8 having three stator blades 76, 77, 78 each having a major surface 90 that is curved along the entire length of the blade.

With further reference to FIG. 6, outer edge 82 contains an angling portion 92 having an angle that extends toward longitudinal axis 70 and in a direction toward outflow port 28. Inner wall 24 contains a constricting portion 94 within second part 18 such that blood flow conduit 21 constricts in that region. The constricting of blood flow conduit 21 can proceed in a direction toward outflow port 28. In addition, the region of blood flow conduit 21 containing constricting portion 94 can contain at least a portion of angling portion 92. For example, angling portion 92 can be within the constricting region of blood flow conduit 21 defined by constricting portion 94.

As also shown in FIG. 6, inner edge 84 can contain an angling portion 96 having an angle that extends toward longitudinal axis 70 and in a direction toward outflow port 28. Stator hub 80 can contain a tapering portion 202 having a taper that proceeds toward longitudinal axis 70 and in a direction toward outflow port 28. In addition, inner wall 24 can contain an expanding portion 104 within outflow portion 20 such that blood flow conduit 21 expands in that region. The expanding of blood flow conduit 21 can proceed in a direction toward outflow port 28. It is noted that the net result of the constricting portion 94 and the tapering portion 202 creates a blood flow field having a cross-sectional area that increases, at least at some point, in the direction toward outflow port 28.

Collectively, the angling portion 92 of outer edge 82, constricting portion 94 of inner wall 24, angling portion 96 of inner edge 84, tapering portion 202 of stator hub 80, and expanding portion 104 of inner wall 24 gradually change and reduce blood flow velocities within blood flow channel 22 of pump 200 such that blood damage is minimized. Like pump 10, pump 200 can achieve these gradual velocity changes with an overall length that is shorter than the length required for a pump not using the configurations described herein. Again, the gradual re-orientation of tangential blood flow is accomplished primarily by the structure and position of stator blades 76, 78. For example, the curved portion of each stator blade 76, 78 forces tangentially moving blood to move in a more axial direction. The gradual reduction of axial blood flow velocity, resulting in a conversion of the blood's kinetic energy to static pressure, is accomplished by the expansion of the cross-sectional area of the blood flow field within the blood flow conduit 21 from rotor element 30 to outflow port 28. For example, as the cross-sectional blood flow field area increases, blood flow velocity decreases and static pressure increases. In addition, the blood flow field within this region of blood flow conduit 21 is well-organized and uniform such that regions of stagnation, separation, or recirculation are reduced or eliminated.

Blood pumps having slanting outflow components as described herein with respect to FIGS. 2 and 6 can be readily manufactured. Again, each blood pump component can be constructed from materials that are compatible with implantation. For example, titanium metal can be used to make, without limitation, a stator hub, outflow stator blade, and an inner wall of a blood flow conduit.

Manufacture of both a stator blade component having an angling outer edge and a blood flow conduit component having a constricting inner diameter can be such that the two components fit together to form a taper-lock configuration. Briefly, with reference to FIGS. 2 and 6, outflow bearing 38, stator hub 80, and outflow stator blades 76, 78 can be assembled into a first component of a taper-lock configuration and second part 18 having inner wall 24 with constricting portion 94 can be a second component. As this first component is inserted into the second component, the outer edge 84 of the stator blades can come into contact with inner wall 24 in the region of constricting portion 94. Thus, the insertion and compression of this first component into the second component can result in the abutment of outer edge 84 of the stator blades with inner wall 24 in the region of constricting portion 94 such that an interface is formed between the two components. Such contact can firmly position outflow bearing 38, stator hub 80, and outflow stator blades 76, 78 within blood flow conduit 21. If desired, this taper-lock configuration can be fortified by conventional attachment techniques such as welding, cross-pinning, or set screws. For example, second part 18 can contain set screw 106 for applying pressure to inner wall 24 such that outflow bearing 38, stator hub 80, and outflow stator blades 76, 78 are more secure within blood flow conduit 21. In addition, a firm fit can prevent longitudinal and rotational movement of these structures within blood flow channel 22 during pump operation as well as reduce the chance of producing gaps or discontinuities between outer edge 84 and inner wall 24.

A pump housing having a blood flow conduit with a constricting inner diameter can be fabricated as one unit, or multiple units that are assembled. For example, constricting portion 94 can be made as one unit with second part 18 of blood flow conduit 21, or constricting portion 94 can be made as a separate piece that is inserted into a non-constricting second part 18 of blood flow conduit 21 to form a blood flow conduit having a constricting inner diameter. Likewise, blood flow conduit 21 having an expanding inner diameter can be fabricated as one unit, or multiple units that are assembled. For example, expanding portion 104 can be made as a single unit with outflow portion 20 or as a separate piece that is inserted into an outflow portion 20, having a slightly larger and constant inner diameter to form an outflow portion with an expanding portion.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An axial flow blood pump comprising:
   a pump housing having a blood flow conduit with an inflow port for receiving blood and an outflow port for expelling blood;
   an inflow bearing disposed within the blood flow conduit at a position proximal the inflow port;
   an outflow bearing disposed within the blood flow conduit at a position proximal the outflow port;
   an electromagnetic rotor element having an inflow end on a side of the electromagnetic rotor element proximal the inflow port, an outflow end on a side of the electromagnetic rotor element proximal the outflow port, and a longitudinal axis extending through the inflow end of the electromagnetic rotor element and the outflow end of the electromagnetic rotor element, the inflow end being rotatably mounted to the inflow bearing, and the outflow end being rotatably mounted to the outflow bearing, wherein the inflow bearing and the outflow bearing support the electromagnetic rotor element for rotation within the blood flow conduit about the longitudinal axis of the electromagnetic rotor element;
   a motor stator element that generates electromagnetic force, the motor stator element being oriented such that the electromagnetic force actuates the electromagnetic rotor element to rotate within the blood flow conduit about the longitudinal axis of the electromagnetic rotor element;
   an impeller mechanism coupled to the electromagnetic rotor element such that the impeller mechanism rotates upon actuation of the electromagnetic rotor element, the impeller mechanism comprising a blade structure being oriented to facilitate movement of blood from the inflow port to the outflow port of the blood flow conduit upon rotation of the impeller mechanism; and
   an outflow stator blade disposed within the blood flow conduit and adjacent the outflow end of the electromagnetic rotor element, the outflow stator blade comprising an outer edge disposed on a side of the outflow stator blade proximal an inner wall of the blood flow conduit, an inner edge disposed on a side of the outflow stator blade proximal the longitudinal axis of the electromagnetic rotor element, and a major surface extending from the outer edge of the outflow stator blade to the inner edge of the outflow stator blade, wherein at least a portion of the outer edge of the outflow stator blade extends at an angle toward the longitudinal axis of the electromagnetic rotor element.

2. The axial flow blood pump of claim 1, wherein the portion of the outer edge of the outflow stator blade extending at an angle toward the longitudinal axis of the electromagnetic rotor element extends toward the outflow port of the blood flow conduit.

3. The axial flow blood pump of claim 1, wherein at least a portion of the inner edge of the outflow stator blade extends at an angle toward the longitudinal axis of the electromagnetic rotor element.

4. The axial flow blood pump of claim 3, wherein the portion of the inner edge of the outflow stator blade extending at an angle toward the longitudinal axis of the electromagnetic rotor element extends toward the outflow port of the blood flow conduit.

5. The axial flow blood pump of claim 1, wherein at least a portion of the major surface of the outflow stator blade is curved.

6. The axial flow blood pump of claim 1, wherein at least a portion of the outer edge of the outflow stator blade contacts the inner wall of the blood flow conduit.

7. The axial flow blood pump of claim 1, wherein at least a portion of the outflow stator blade extends beyond the outflow bearing toward the inflow port, the extending portion of the outflow stator blade being oriented between the inner wall of the blood flow conduit and the electromagnetic rotor element.

8. The axial flow blood pump of claim 1, wherein at least a portion of the blood flow conduit has an inner diameter that constricts.

9. The axial flow blood pump of claim 8, wherein the constriction proceeds toward the outflow port of the blood flow conduit.

10. The axial flow blood pump of claim 8, wherein the portion of the blood flow conduit having the constricting inner diameter contains at least a portion of the outflow stator blade.

11. The axial flow blood pump of claim 1, further comprising a stator hub oriented within the blood flow conduit between the electromagnetic rotor element and the outflow port, wherein at least a portion of the stator hub tapers at an angle toward the longitudinal axis of the electromagnetic rotor element.

12. The axial flow blood pump of claim 11, wherein the tapering portion of the stator hub proceeds toward the outflow port of the blood flow conduit.

13. The axial flow blood pump of claim 12, wherein at least a portion of the blood flow conduit has an inner diameter that constricts.

14. The axial flow blood pump of claim 13, wherein the constriction proceeds toward the outflow port of the blood flow conduit.

15. The axial flow blood pump of claim 14, wherein at least a portion of a cross-sectional blood flow field area defined within the portion of the blood flow conduit having the constricting inner diameter increases in a direction toward the outflow port.

16. The axial flow blood pump of claim 1, wherein the blood flow conduit comprises an inflow portion containing the inflow port, a central portion containing at least a portion of the electromagnetic rotor element, and an outflow portion containing the outflow port, wherein at least a portion of the outflow portion of the blood flow conduit has an inner diameter that expands.

17. The axial flow blood pump of claim 16, wherein the expansion proceeds toward the outflow port of the blood flow conduit.

18. The axial flow blood pump of claim 1, wherein at least a portion of the electromagnetic rotor element tapers at an angle toward the longitudinal axis of the electromagnetic rotor element.

19. The axial flow blood pump of claim 18, wherein the tapering portion of the electromagnetic rotor element proceeds toward the outflow port of the blood flow conduit.

20. The axial flow blood pump of claim 19, wherein at least a portion of the blood flow conduit has an inner diameter that constricts.

21. The axial flow blood pump of claim 20, wherein the constriction proceeds toward the outflow port of the blood flow conduit.

22. The axial flow blood pump of claim 21, wherein at least a portion of a cross-sectional blood flow field area defined within the portion of the blood flow conduit having the constricting inner diameter increases in a direction toward the outflow port.

23. An axial flow blood pump comprising:
a pump housing having a blood flow conduit with an inflow port for receiving blood and an outflow port for expelling blood, the blood flow conduit having an inner wall defining an inner diameter of the blood flow conduit, wherein at least a portion of the inner diameter of the blood flow conduit constricts, and at least a portion of the cross-sectional blood flow field area defined within the portion of the blood flow conduit having the constricting inner diameter increases in a direction toward the outflow port;
an inflow bearing disposed within the blood flow conduit at a position proximal the inflow port;
an outflow bearing disposed within the blood flow conduit at a position proximal the outflow port;
an electromagnetic rotor element having an inflow end on a side of the electromagnetic rotor element proximal the inflow port, an outflow end on a side of the electromagnetic rotor element proximal the outflow port, and a longitudinal axis extending through the inflow end of the electromagnetic rotor element and the outflow end of the electromagnetic rotor element, the inflow end being rotatably mounted to the inflow bearing, and the outflow end being rotatably mounted to the outflow bearing, wherein the inflow bearing and the outflow bearing support the electromagnetic rotor element for rotation within the blood flow conduit about the longitudinal axis of the electromagnetic rotor element;
a motor stator element that generates electromagnetic force, the motor stator element being oriented such that the electromagnetic force actuates the electromagnetic rotor element to rotate within the blood flow conduit about the longitudinal axis of the electromagnetic rotor element;
an impeller mechanism coupled to the electromagnetic rotor element such that the impeller mechanism rotates upon actuation of the electromagnetic rotor element, the impeller mechanism comprising a blade structure being oriented to facilitate movement of blood from the inflow port to the outflow port of the blood flow conduit upon rotation of the impeller mechanism; and
an outflow stator blade disposed within the blood flow conduit and adjacent the outflow end of the electromagnetic rotor element.

24. The axial flow blood pump of claim 23, wherein the constriction of the inner diameter proceeds toward the outflow port of the blood flow conduit.

25. The axial flow blood pump of claim 23, wherein the portion of the blood flow conduit having the constricting inner diameter contains at least a portion of the outflow stator blade.

26. The axial flow blood pump of claim 23, wherein the outflow stator blade comprises an outer edge disposed on a side of the outflow stator blade proximal the inner wall of the blood flow conduit, an inner edge disposed on a side of the outflow stator blade proximal the longitudinal axis of the electromagnetic rotor element, and a major surface extending from the outer edge of the outflow stator blade to the inner edge of the outflow stator blade, wherein at least a portion of the outer edge of the outflow stator blade extends at an angle toward the longitudinal axis of the electromagnetic rotor element.

27. The axial flow blood pump of claim 26, wherein the portion of the outer edge of the outflow stator blade extending at an angle toward the longitudinal axis of the electromagnetic rotor element extends toward the outflow port of the blood flow conduit.

28. The axial flow blood pump of claim 26, wherein at least a portion of the inner edge of the outflow stator blade extends at an angle toward the longitudinal axis of the electromagnetic rotor element.

29. The axial flow blood pump of claim 28, wherein the portion of the inner edge of the outflow stator blade extending at an angle toward the longitudinal axis of the electromagnetic rotor element extends toward the outflow port of the blood flow conduit.

30. The axial flow blood pump of claim 26, wherein at least a portion of the major surface of the outflow stator blade is curved.

31. The axial flow blood pump of claim 26, wherein at least a portion of the outer edge of the outflow stator blade contacts the inner wall of the blood flow conduit.

32. The axial flow blood pump of claim 23, wherein at least a portion of the outflow stator blade extends beyond the outflow bearing toward the inflow port, the extending portion of the outflow stator blade being oriented between the inner wall of the blood flow conduit and the electromagnetic rotor element.

33. The axial flow blood pump of claim 23, further comprising a stator hub oriented within the blood flow conduit between the electromagnetic rotor element and the outflow port, wherein at least a portion of the stator hub tapers at an angle toward the longitudinal axis of the electromagnetic rotor element.

34. The axial flow blood pump of claim 33, wherein the tapering portion of the stator hub proceeds toward the outflow port of the blood flow conduit.

35. The axial flow blood pump of claim 23, wherein the blood flow conduit comprises an inflow portion containing the inflow port, a central portion containing at least a portion of the electromagnetic rotor element, and an outflow portion containing the outflow port, wherein at least a portion of the outflow portion of the blood flow conduit has an inner diameter that expands.

36. The axial flow blood pump of claim 35, wherein the expansion proceeds toward the outflow port of the blood flow conduit.

37. The axial flow blood pump of claim 23, wherein at least a portion of the electromagnetic rotor element tapers at an angle toward the longitudinal axis of the electromagnetic rotor element.

38. The axial flow blood pump of claim 37, wherein the tapering portion of the electromagnetic rotor element proceeds toward the outflow port of the blood flow conduit.

39. An axial flow blood pump comprising:

a blood flow conduit;

a rotor element having an inflow end, an outflow end, and a longitudinal axis extending through the inflow and outflow ends, the rotor element being suspended for rotation within the blood flow conduit about the longitudinal axis;

a motor stator oriented to rotate the rotor element;

an impeller blade coupled to the rotor element and oriented to facilitate movement of blood through the blood flow conduit upon rotation of the rotor element; and an outflow stator blade disposed within the blood flow conduit and adjacent the outflow end of the rotor element, the outflow stator blade comprising an outer edge disposed on a side of the outflow stator blade proximal an inner wall of the blood flow conduit and an inner edge disposed on a side of the outflow stator blade proximal the longitudinal axis of the rotor element, wherein at least a portion of the outer edge of the outflow stator blade extends at an angle toward the longitudinal axis of the rotor element.

40. The axial flow blood pump of claim 39, wherein the portion of the outer edge of the outflow stator blade extending at an angle toward the longitudinal axis of the electromagnetic rotor element extends toward an outflow port of the blood flow conduit.

41. The axial flow blood pump of claim 39, wherein at least a portion of the inner edge of the outflow stator blade extends at an angle toward the longitudinal axis of the electromagnetic rotor element.

42. The axial flow blood pump of claim 39, wherein at least a portion of the blood flow conduit has an inner diameter that constricts.

43. The axial flow blood pump of claim 42, further comprising a stator hub oriented within the blood flow conduit between the electromagnetic rotor element and an outflow port, wherein at least a portion of the stator hub tapers at an angle toward the longitudinal axis of the electromagnetic rotor element.

44. The axial flow blood pump of claim 42, wherein at least a portion of the electromagnetic rotor element tapers at an angle toward the longitudinal axis of the electromagnetic rotor element.

45. The axial flow blood pump of claim 42, wherein at least a portion of a cross-sectional blood flow field area defined within the portion of the blood flow conduit having the constricting inner diameter increases in a direction toward the outflow port.

46. The axial flow blood pump of claim 39, wherein the blood flow conduit comprises an outflow portion containing an outflow port, wherein at least a portion of the outflow portion of the blood flow conduit has an inner diameter that expands.

47. An axial flow blood pump comprising:

a blood flow conduit with an inflow port for receiving blood and an outflow port for expelling blood, the blood flow conduit having an inner wall defining an inner diameter of the blood flow conduit, wherein at least a portion of the inner diameter of the blood flow conduit constricts, and at least a portion of the cross-sectional blood flow field area defined within the portion of the blood flow conduit having the constricting inner diameter increases in a direction toward the outflow port;

a rotor element oriented to rotate within the blood flow conduit;

a motor stator oriented to rotate the rotor element;

an impeller blade coupled to the rotor element and oriented to facilitate movement of blood through the blood flow conduit upon rotation of the rotor element; and an outflow stator blade disposed within the blood flow conduit and adjacent the outflow end of the rotor element.

48. The axial flow blood pump of claim 47, wherein the constriction proceeds toward the outflow port of the blood flow conduit.

49. The axial flow blood pump of claim 47, wherein the outflow stator blade comprises an outer edge disposed on a side of the outflow stator blade proximal the inner wall of the blood flow conduit, an inner edge disposed on a side of the outflow stator blade proximal a longitudinal axis of the electromagnetic rotor element, and a major surface extending from the outer edge of the outflow stator blade to the inner edge of the outflow stator blade, wherein at least a portion of the outer edge of the outflow stator blade extends at an angle toward the longitudinal axis of the electromagnetic rotor element.

50. The axial flow blood pump of claim 49, wherein the portion of the outer edge of the outflow stator blade extending at an angle toward the longitudinal axis of the electromagnetic rotor element extends toward the outflow port of the blood flow conduit.

51. The axial flow blood pump of claim 49, wherein at least a portion of the inner edge of the outflow stator blade extends at an angle toward the longitudinal axis of the electromagnetic rotor element.

52. The axial flow blood pump of claim 49, wherein at least a portion of the outer edge of the outflow stator blade contacts the inner wall of the blood flow conduit.

53. The axial flow blood pump of claim 47, further comprising a stator hub oriented within the blood flow conduit between the electromagnetic rotor element and the outflow port, wherein at least a portion of the stator hub tapers at an angle toward a longitudinal axis of the electromagnetic rotor element.

54. The axial flow blood pump of claim 47, wherein the blood flow conduit comprises an outflow portion containing the outflow port, wherein at least a portion of the outflow portion of the blood flow conduit has an inner diameter that expands.

55. The axial flow blood pump of claim 47, wherein at least a portion of the electromagnetic rotor element tapers at an angle toward a longitudinal axis of the electromagnetic rotor element.

* * * * *